United States Patent [19]

Laurent

[11] 4,047,050

[45] Sept. 6, 1977

[54] CALIBRATING IMPULSE GENERATOR FOR AN IMPULSE-SHAPING ELEMENT

[75] Inventor: Estan Laurent, Lidingo, Sweden

[73] Assignee: Siemens Aktiengesellschaft, Berlin & Munich, Germany

[21] Appl. No.: 624,559

[22] Filed: Oct. 21, 1975

[30] Foreign Application Priority Data

Nov. 7, 1974   Germany .......................... 2452933

[51] Int. Cl.² ............................................. H05K 3/00
[52] U.S. Cl. ............................ 307/108; 128/2.05 R; 128/2.05 D
[58] Field of Search ................ 128/2.05 R, 2.05 D, 128/2.05 E; 328/127, 181, 185; 307/228, 229, 230, 106, 108

[56] References Cited

U.S. PATENT DOCUMENTS

| 3,521,082 | 7/1970 | Wolk | 328/185 |
| 3,772,533 | 11/1973 | Bruckner | 307/229 |

OTHER PUBLICATIONS

Winter et al., "A Simple Cardiac Contractility Computer", Medical and Biological Eng., vol. II, No. 5, Sept. 1973, pp. 560–568.
King et al., "A Simple Calibrator for Measuring the First Derivative of Pressure Wave Forms", IEEE Transactions on Biomedical Engineering, vol. BME 19, No. 4, July 1972, pp. 320–321.

*Primary Examiner*—David Smith, Jr.
*Attorney, Agent, or Firm*—Hill, Gross, Simpson, Van Santen, Steadman, Chiara & Simpson

[57] ABSTRACT

A calibrating impulse generator which is connectable to the input of a signal-shaping element, the latter of which reshapes the input signal in comformance with the function $$\frac{df(t)}{dt} / f(t).$$

The calibrating impulse generator is constructed, whereby a calibrating impulse proceeds over a period of time from an initial value in accordance with an *e*-function to a final value, and after reaching the final value return again to its initial value. Calibrating impulses with the described sequence will produce rectangular or square-wave impulses of known amplitude at the output of the signal-shaping element.

3 Claims, 4 Drawing Figures

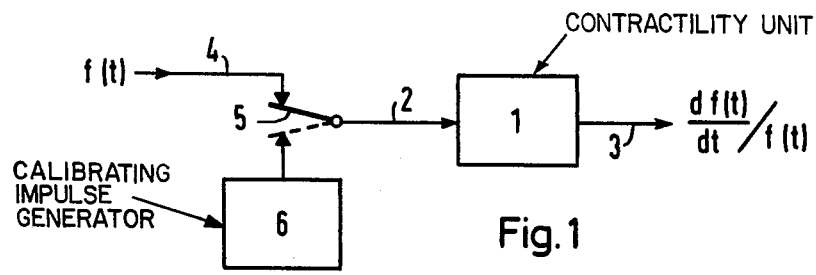
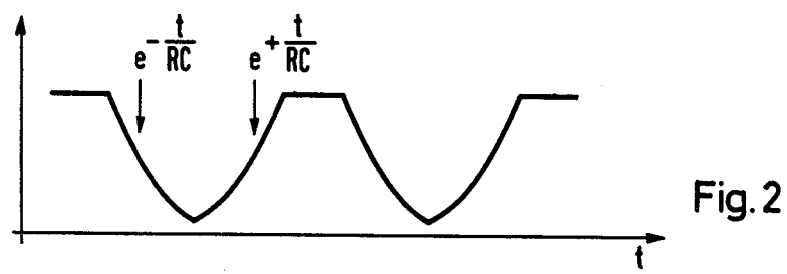
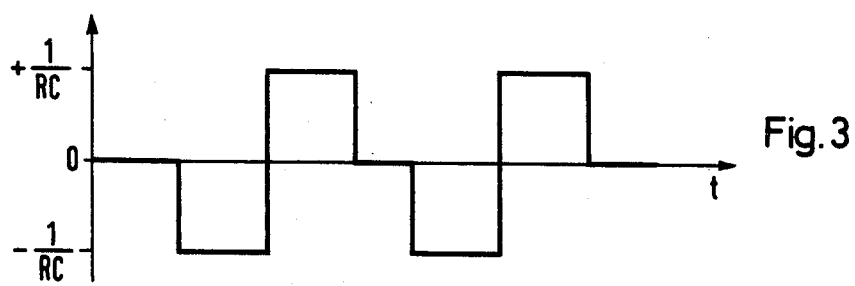
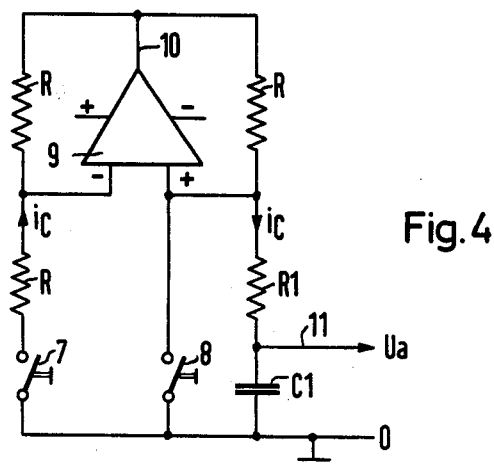

CALIBRATING IMPULSE GENERATOR FOR AN IMPULSE-SHAPING ELEMENT

FIELD OF THE INVENTION

The present invention relates to a calibrating impulse generator for a signal-shaping element.

More particularly, the present invention relates to a calibrating impulse generator which is connectable to the input of a signal-shaping element, the latter of which reshapes the input signal in conformance with the function $$\frac{df(t)}{dt} / f(t).$$

A signal-shaping element which reshapes its input signal in accordance with the above-mentioned function may be utilized, for example, in the measurement of the contractibility of the heart. The primary function $f(t)$ which is conducted from the heart as an electrical signal for example, may embody the left chamber pressure, or may correspond to the apex or peak impulses.

In a signal-shaping element of the mentioned type, there consists the requirement that a calibration be possible, meaning, that a known input voltage may be supplied thereto which leads to an impulse of known amplitude at the output of the signal-shaping element. Thereby, the difficulty must be overcome in creating a calibrating impulse generator which delivers calibrating impulses at a timed cycle which, after reshaping in the signal-shaping element, will lead to utilizable calibrating impulses at the output of the signal-shaping element.

DISCUSSION OF THE PRIOR ART

A differentiating amplifier is currently known wherein there is employed a calibrating signal for effecting the calibration thereof, which evinces the shape of a triangle or, respectively, a trapezoid with at least one flattened edge. However, the calibrating signal which is used in this differential amplifier is not utilizable in a signal-shaping element in accordance with the concept of the present invention and which by itself divides the differentiated input signal through the input signal.

SUMMARY OF THE INVENTION

Accordingly, it is an object of the present invention to provide a calibrating impulse generator for a signal-shaping element which will reshape the calibrating signal in conformance with the function $$\frac{df(t)}{dt} / f(t).$$

The foregoing object is inventively attained through such a construction of the calibrating impulse generator, whereby a calibrating impulse proceeds over a period of time from an initial value in accordance with an e-function to a final value, and after reaching the final value returns again to its initial value. The return of the signal may be a mirror-image of the e-function. The invention is predicated on the knowledge that calibrating impulses with the described sequence will produce rectangular or square-wave impulses of known amplitude at the output of the signal-shaping element, These square-wave impulses thus allow for an exact determination of the amplitudes of the output signals of the signal-shaping element, which is branched off from a physiological input signal, and further allows for a testing or supervision of the signal-shaping element.

BRIEF DESCRIPTION OF THE DRAWINGS

Further advantages and details of the invention may now be ascertained from the following description of an exemplary embodiment thereof, taken in conjunction with the accompanying drawings; in which:

FIG. 1 schematically illustrates a calibrating impulse generator for elucidating the concept of the present invention;

FIGS. 2 and 3 respectively show the signal time cycle at different locations of the arrangement pursuant to FIG. 1; and FIG. 4 illustrates the circuit of the calibrating impulse generator which is schematically shown in FIG. 1.

DETAILED DESCRIPTION

Illustrated in FIG. 1 is a contractibility unit 1, in effect, a unit for measuring contractions, which reshapes the signal at its input 2 in conformance with the function $$\frac{df(t)}{dt} / f(t).$$

The output signal at the output 3 also proceeds pursuant to this function in dependence upon the input signal. The contractibility unit 1, for example, may serve for the determination of a signal which is representative of the left chamber pressure of the heart, or for the determination of the apex impulses. The physiological measurement signal is delivered to the conductor 4 and is transmissible to the contractibility unit 1 through the intermediary of a calibrating switch 5. The calibration of the contractibility unit 1 is carried out when the calibrating switch 5 is switched over into the position illustrated in phantom-lines. In this position the switch connects the input 2 of the contractibility unit 1 with a calibrating impulse generator 6.

FIG. 2 illustrates the sequence or cycle of the output impulses of the calibrating impulse generator 6. The descending sides or slopes of the output impulses proceed pursuant to the function $e^{-t/RC}$ and the rising sides or slopes of the impulses pursuant to the function $e^{t/RC}$. For example, during calibration the function $f(t) = e^{-t/RC}$ is also valid for the descending slopes of the input impulses. Through differentiation of the calibrating impulses in the contractibility unit 1 there is thus obtained $$\frac{df(t)}{dt} = \frac{-1}{RC} \cdot e^{\frac{-t}{RC}}.$$

When the final output signal is then formed through division with $f(t)$, there is then obtained for the output signal of the contractibility unit 1 the function $-1/RC$. The descending slope of a calibrating impulse thus corresponds to a negative square-wave impulse at the output 3 of the contractibility unit 1. Correspondingly, during the rising slope of a calibrating impulse at the input 2, there is received a positive square-wave impulse at the output 3. The amplitudes of the square-wave impulses are $-1/RC$ and $1/RC$. Their cycle is illustrated in FIG. 3 of the drawings. By means of the described selection of the cycle of the calibrating impulses, there are thus obtained positive and negative square-wave impulses at the output 3 which facilitate a precise calibration. Within the scope of the invention, depending upon circumstances, the formation of square-wave impulses of only a single polarity may be sufficient.

Illustrated in FIG. 4 of the drawings is an example of the circuit for the calibrating impulse generator 6. The calibrating impulse generator 6 contains two calibrating push-buttons 7 and 8. The calibrating push-button 7 is connected across a resistor R to the negative input of an operational amplifier 9, whereas the calibrating push-button 8 is located directly on the positive input of this amplifier. The output 10 of the operational amplifier 9 is connected across two equally sized resistors R with the positive and with the negative input. Located between the positive input and ground is further the series circuit formed of a resistor $R_1$ and a capacitance $C_1$. The calibrating voltage is tapped off at the capacitance C1, and namely at output 11. It lies between the output 11 and ground.

After repositioning of the calibrating switch 5, for producing the rising slope of the calibrating impulse, there is now closed the switch 7. For $i_c$ the following is then valid:

$$i_c = Ua/(R-R1) \text{ while } R \cdot i_c = Ua + R1 \cdot i_c$$

For $i_c$ there is further valid:
$$i_c = C1 \cdot (dUa/dt)$$

from which there follows:

$$\frac{Ua}{R-R1} = C1 \cdot \frac{dUa}{dt}$$

$$Ua = e^{\frac{1}{(R-R1)C1}} + \text{const.}$$

For $R = 2R1$ there becomes $$Ua = e^{1/R1C1} + \text{const.}$$

When the switch 7 is opened again, $i_c$ immediately becomes zero and Ua = constant. During this phase, the output voltage thus corresponds to the direct voltage components between the rising and the descending slopes or sides of the calibrating impulses pursuant to FIG. 2.

When the switch 8 is thereafter closed, the capacitance C1 is discharged and the following relationship is valid:

$$Ua = \text{const.} \cdot e^{\frac{-t}{R1\,C1}}$$

The output voltage at output 11 thus proceeds exactly in accordance with FIG. 2 and may be utilized for the calibration of the contractibility unit 1.

While there has been shown what is considered to be the preferred embodiment of the invention, it will be obvious that modifications may be made which come within the scope of the disclosure of the specification.

What is claimed is:

1. A calibrating impulse generator including a signal-shaping element having an input for receiving an input signal $f(t)$ and being operative for reshaping the input signal pursuant to a function represented by the quotient of the derivative with respect to time of the input signal, and the input signal, the quotient thus being expressed:

$$(\frac{df(t)}{dt} / f(t)),$$

the improvement comprising said calibrating inpulse generator having a calibrating impulse generating circuit with an output connected to the input of said signal-shaping element, said calibrating impulse generating circuit having a construction for supplying a calibrating impulse to said output which proceeds from an initial value pursuant to an e-function over a period of time to a final value and after reaching the final value returns again to its initial value, said calibrating impulse returning from said final value to its initial value pursuant to an e-function which is a mirror-image to the e-function pursuant to which said signal proceeds from its initial value to its final value.

2. A calibrating impulse generator as claimed in claim 1, each said impulse having a direct-voltage component of constant amplitude intermediate its rising and descending side slopes.

3. A calibrating impulse generator including a signal-shaping element having an input for receiving an input signal $f(t)$, said element reshaping the input signal at the input thereof pursuant to the function $$\frac{df(t)}{dt} / f(t),$$

the improvement comprising: said calibrating impulse generator having an impulse generating circuit connected to said input of said element and said circuit being of a construction so that a calibrating impulse proceeds from an initial value pursuant to an e-function over a period of time to a final value and after reaching the final value returns again to its initial value, said impulse generating circuit comprising a capacitance for producing said e-function; and means for charging and discharging said capacitance, and said circuit further comprising an ohmic charging resistor being connected to said capacitance at which the calibrating impulses are branched off; an operational amplifier, said capacitance being connected in series with said ohmic resistor to a first input of said operational amplifier and with one pole connected to ground; a plurality of equally-sized coupling resistors being connected between the output and two inputs of said operational amplifier; a first calibrating switch being connected between the first input of said operational amplifier and ground; and a second calibrating switch and one said coupling resistor forming a series circuit between the second input of said operational amplifier and ground, said coupling resistors being twice as large as said ohmic charging resistor.

* * * * *